US00PP19321P2

(12) United States Plant Patent
Davasse

(10) Patent No.: US PP19,321 P2
(45) Date of Patent: Oct. 14, 2008

(54) ***FORSYTHIA* PLANT NAMED 'MINDOR'**

(50) Latin Name: *Forsythia×intermedia*
Varietal Denomination: Mindor

(75) Inventor: Jean-Paul Davasse, Beaufort-en-Vallee (FR)

(73) Assignee: Spring Meadow Nursery Inc., Grand Haven, MI (US)

( * ) Notice: Subject to any disclaimer, the term of this patent is extended or adjusted under 35 U.S.C. 154(b) by 283 days.

(21) Appl. No.: 11/324,507

(22) Filed: Dec. 31, 2005

(51) Int. Cl.
*A01H 5/00* (2006.01)

(52) U.S. Cl. ..... Plt./230

(58) Field of Classification Search ..... Plt./230
See application file for complete search history.

*Primary Examiner*—Kent L. Bell
*Assistant Examiner*—Georgia Helmer
(74) *Attorney, Agent, or Firm*—C. A. Whealy

(57) ABSTRACT

A new and distinct cultivar of *Forsythia* plant named 'Mindor', characterized by its upright and somewhat outwardly spreading plant habit; freely branching growth habit; dark green-colored foliage; and numerous bright yellow-colored flowers.

2 Drawing Sheets

Botanical designation: *Forsythia×intermedia.*
Cultivar denomination: 'Mindor'.

BACKGROUND OF THE INVENTION

The present Invention relates to a new and distinct cultivar of *Forsythia* plant, botanically known as *Forsythia× intermedia,* and hereinafter referred to by the cultivar name Mindor.

The new *Forsythia* is a naturally-occurring branch mutation of the *Forsythia×intermedia* cultivar Fiesta, disclosed in U.S. Plant Pat. No. 7,523. The new *Forsythia* was discovered and selected by the Inventor in a controlled environment in Angers, France on Mar. 15, 1997 from within a population of plants of the cultivar Fiesta.

Asexual reproduction of the new cultivar by softwood cuttings in Angers, France has shown that the unique features of this new *Forsythia* are stable and reproduced true to type in successive generations.

SUMMARY OF THE INVENTION

Plants of the cultivar Mindor have not been observed under all possible environmental conditions. The phenotype may vary somewhat with variations in environment such as temperature and light intensity without, however, any variance in genotype.

The following traits have been repeatedly observed and are determined to be the unique characteristics of 'Mindor'. These characteristics in combination distinguish 'Mindor' as a new and distinct *Forsythia* cultivar:

1. Upright and somewhat outwardly spreading plant habit.
2. Freely branching growth habit.
3. Dark green-colored foliage.
4. Numerous bright yellow-colored flowers.

Plants of the new *Forsythia* differ primarily from plants of the parent, the cultivar Fiesta, in the following characteristics:

1. Plants of the new *Forsythia* are larger than plants of the cultivar Fiesta.

2. Plants of the new *Forsythia* have dark green-colored leaves whereas plants of the cultivar Fiesta have variegated leaves.
3. Leaves of plants of the new *Forsythia* are thick and flat whereas leaves of plants of the cultivar Fiesta are thin, rugose and undulating.
4. Plants of the new *Forsythia* are more freely and uniformly flowering than plants of the cultivar Fiesta.

Plants of the new *Forsythia* can be compared to plants of the cultivar Lynwood, not patented. In side-by-side comparisons conducted in Grand Haven, Mich., plants of the new *Forsythia* differed from plants of the cultivar Lynwood in the following characteristics:

1. Plants of the new *Forsythia* were much shorter than plants of the cultivar Lynwood.
2. Leaves of plants of the new *Forsythia* were flat, elliptic in shape and had entire margins whereas leaves of plants of the cultivar Lynwood were folded at the midrib, lanceolate in shape and had serrated margins.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Forsythia.*

The photograph at the bottom of the sheet comprises a side perspective view of a typical plant of 'Mindor' grown in a container.

The photograph at the top of the sheet is a close-up view of typical flowering stems of 'Mindor'.

The photograph on the second sheet is a close-up view of typical leaves of 'Mindor'.

DETAILED BOTANICAL DESCRIPTION

Plants of the cultivar Mindor have not been observed under all possible environmental conditions. The phenotype may vary somewhat with variations in environment such as temperature and light intensity, without, however, any variance in genotype. The aforementioned photographs and following observations and measurements describe plants grown during the spring and summer in Grand Haven, Mich., under commercial practice in an outdoor nursery. Plants used for the photographs and description were about three years old. In the following description, color references are made to The Royal Horticultural Society Colour Chart, 1995 Edition, except where general terms of ordinary dictionary significance are used.

Botanical classification: *Forsythia×intermedia* cultivar Mindor.

Parentage: Naturally-occurring branch mutation of the *Forsythia×intermedia* cultivar Fiesta, disclosed in U.S. Plant Pat. No. 7,523.

Propagation:

*Type cutting.*—Softwood cuttings.

*Time to initiate roots.*—About two weeks at 27° C.

*Time to produce a rooted young plant.*—About three months at 25° C.

*Root description.*—Fine to thick, fibrous; white in color.

*Rooting habit.*—Freely branching; dense.

Plant description:

*Form.*—Perennial flowering shrub; upright to outwardly spreading plant habit. Freely basal branching habit; about 29 lateral branches per plant; pinching enhances branching.

*Plant height.*—About 82 cm.

*Plant diameter.*—About 75 cm.

*Vigor.*—Vigorous.

*Lateral branches.*—Length: About 82 cm. Diameter: About 4 mm to 5 mm. Internode length: About 4.2 cm. Texture: Smooth, glabrous. Strength: Strong. Color: Between 141A and 137A. Lenticels: Shape: Rounded. Diameter: About 1 mm. Color: Close to 196B.

*Foliage description.*—Arrangement: Opposite, simple. Length: About 7.9 cm. Width: About 3.5 cm. Shape: Elliptic. Apex: Obtuse to acute. Base: Obtuse. Margin: Mostly entire. Aspect: Mostly flat to slightly wavy. Texture, upper and lower surfaces: Smooth, glabrous. Venation pattern: Pinnate. Color: Developing leaves, upper and lower surfaces: 144A. Fully expanded leaves, upper surface: 147A; venation, 147B. Fully expanded leaves, lower surface: 147B; venation, 147B. Petiole length: About 1.1 cm. Petiole diameter: About 2 mm. Petiole texture, upper and lower surfaces: Smooth, glabrous. Petiole color, upper and lower surfaces: 147B.

Flower description:

*Flower type and habit.*—Single axillary funnelform flowers arranged uniformly and densely along the lateral branches. Freely flowering habit, usually about 64 flowers and flower buds per lateral branch. Flowers face mostly outwardly. Flowers not persistent. Flowers slightly fragrant.

*Natural flowering season.*—Flowering begins in the early spring prior to leaf development in Michigan.

*Flower longevity.*—Flowers last about two to three weeks on the plant.

*Flower diameter.*—About 3.5 cm.

*Flower depth.*—About 1.5 cm.

*Flower buds.*—Length: About 4 mm. Diameter: About 3 mm. Shape: Elliptic. Color: 147B.

*Petals.*—Quantity/arrangement: Four per flower fused at the base. Length: About 2 cm. Width: About 1.6 cm. Shape: Oblong. Apex: Obtuse to retuse. Margin: Entire. Texture, upper and lower surfaces: Smooth, glabrous. Color: When opening, upper and lower surfaces: 13A. When opening, upper and lower surfaces: 13A; color becoming closer to 7A with development.

*Sepals.*—Quantity/arrangement: Four fused at the base. Length: About 5 mm. Diameter: About 4 mm. Shape: Elliptic. Apex: Obtuse. Margin: Entire. Sepal texture, upper and lower surfaces: Smooth, glabrous. Color, upper and lower surfaces: 143A.

*Peduncles.*—Length: About 8 mm. Diameter: About 1.5 mm. Strength: Strong. Angle: About 45° from the stem axis. Color: 143A.

*Reproductive organs.*—Androecium: Stamen quantity: Two per flower. Anther size: About 2 mm by 1 mm. Anther shape: Elliptic. Anther color: 7A. Pollen amount: Moderate. Pollen color: 7A. Gynoecium: Pistil quantity: One per flower. Pistil length: About 3 mm. Style length: About 2 mm. Style color: 144A. Stigma shape: Two-parted. Stigma color: 144A. Ovary color: 144A.

*Seeds/fruits.*—Seed and fruit development has not been observed.

Disease/pest resistance: Plants of the new *Forsythia* have not been observed to be resistant to pathogens and pests common to *Forsythia.*

Temperature tolerance: Plants of the new *Forsythia* have been observed to tolerate temperatures from about −20° C. to about 38° C.

It is claimed:

1. A new and distinct cultivar of *Forsythia* plant named 'Mindor', as illustrated and described.

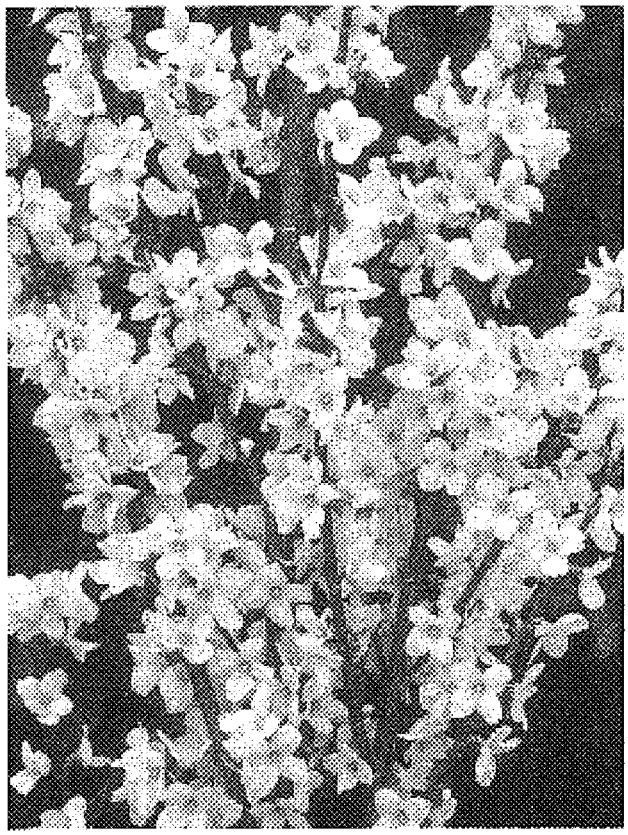
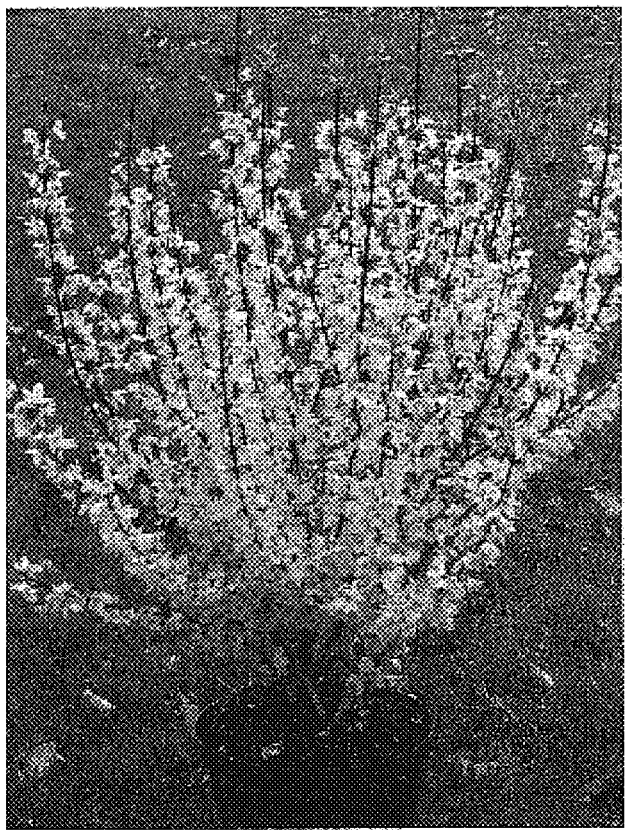

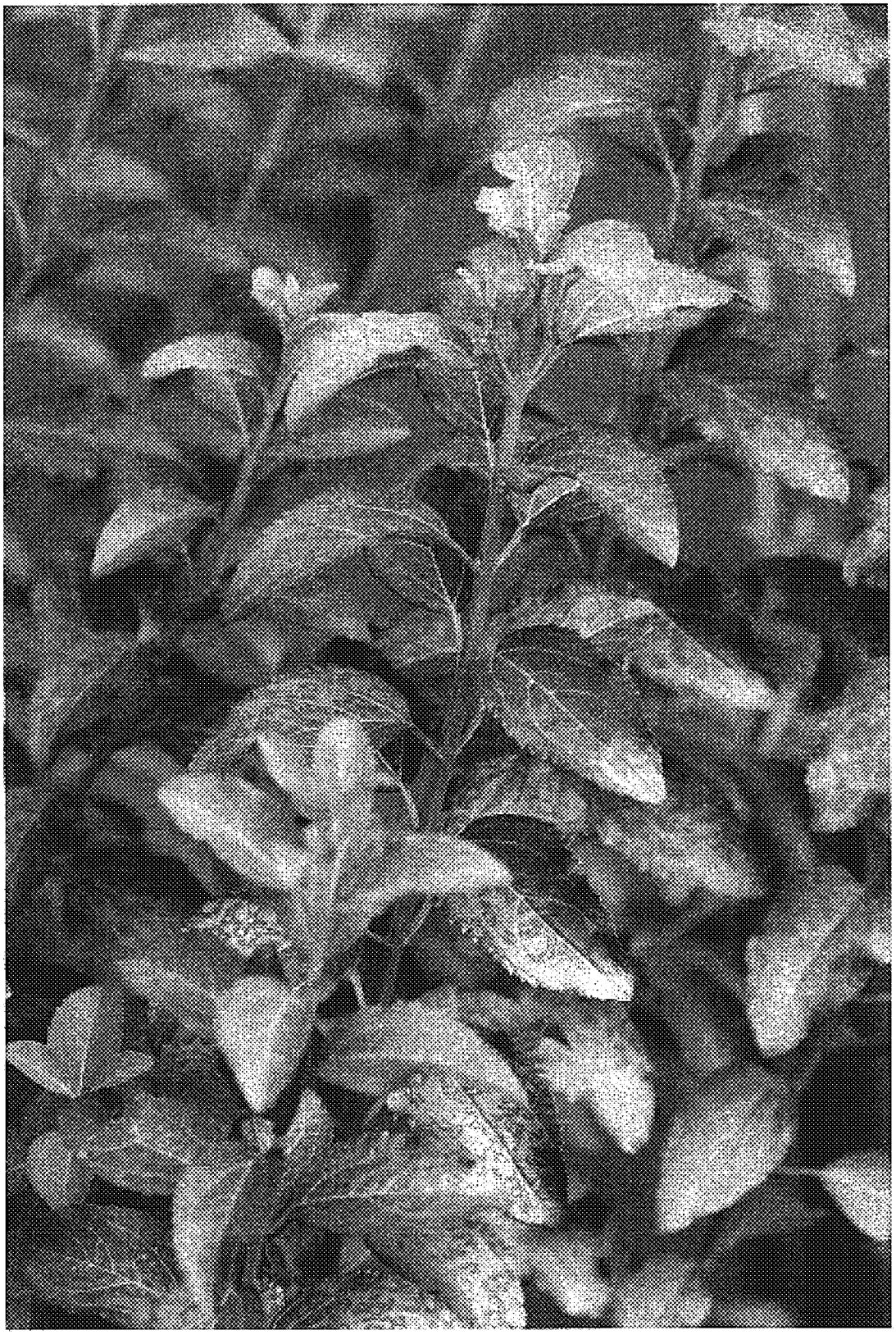

* * * * *